United States Patent [19]
Biftu et al.

[11] Patent Number: 5,326,783
[45] Date of Patent: Jul. 5, 1994

[54] CHOLESTEROL LOWERING COMPOUNDS

[75] Inventors: Tesfaye Biftu, Westfield; Chan-Hwa Kuo, South Plainfield; Conrad Santini, Warren, all of N.J.

[73] Assignee: Merck & Co., Inc., Rahway, N.J.

[21] Appl. No.: 4,875

[22] Filed: Jan. 19, 1993

Related U.S. Application Data

[63] Continuation-in-part of Ser. No. 935,485, Aug. 25, 1992, abandoned.

[51] Int. Cl.$^5$ ................. A61K 31/335; A61K 31/365; C07D 405/06; C07D 319/04
[52] U.S. Cl. .................... 514/452; 549/363; 549/310; 549/60; 549/58; 549/28; 549/23; 548/518; 548/517; 548/455; 548/253; 548/197; 548/187; 544/377; 544/357; 544/336; 544/335; 544/296; 544/295; 544/238; 544/151; 544/61; 544/58.4; 514/422; 514/414; 514/406; 514/397; 514/382; 514/374; 514/365; 514/338; 514/333; 514/321; 514/256; 514/253; 514/233.8; 514/228
[58] Field of Search ............... 549/363, 310, 60, 58, 549/28, 23; 548/518, 517, 455, 197, 187, 253; 514/452, 422, 414, 406, 397, 382, 374, 365, 338, 333, 321, 256, 253, 233.8, 228; 544/377, 357, 336, 335, 296, 295, 238, 151, 61, 58.4

[56] References Cited

U.S. PATENT DOCUMENTS 5,096,923 3/1992 Bergstrom et al. .
5,102,907 4/1992 Bergstrom et al. .
5,132,320 7/1992 Bergstrom et al. .

FOREIGN PATENT DOCUMENTS 0494622 7/1992 European Pat. Off. .
0503520 9/1992 European Pat. Off. .
0512865 11/1992 European Pat. Off. .
WO92/12156 1/1992 PCT Int'l Appl. .
WO92/12157 1/1992 PCT Int'l Appl. .
WO92/12158 1/1992 PCT Int'l Appl. .
WO92/12159 1/1992 PCT Int'l Appl. .
WO92/12160 7/1992 PCT Int'l Appl. .

OTHER PUBLICATIONS

Poulter et al., J. Am. Chem. Soc., 111, 3734–9 (1989).
Corey et al., J. Am. Chem. Soc., 98, 1291–3 (1976).
Ortiz de Montellano, et al., J. Med. Chem., 20, 243–9 (1977).
Dawson et al., J. Antibiotics, 45, 639–47 (1992).
Sidebottom et al., J. Antibiotics, 45, 648–58 (1992).
Jones et al., J. Antibiotics, 45, 1492–98 (1992).
Baxter et al., J. Biol. Chem. 267, 11705–08 (1992).

*Primary Examiner*—Nicky Chan
*Attorney, Agent, or Firm*—Catherine A. Dolan; Carol S. Quagliato; Melvin Winokur

[57] ABSTRACT

This invention is directed to compounds of formula (I) which are novel C3- or C5-acyl sulfonamide, carboxamic acid or tetrazolyl analogs of the Zaragozic acids. These compounds inhibit the enzyme squalene synthase and are useful as cholesterol lowering agents.

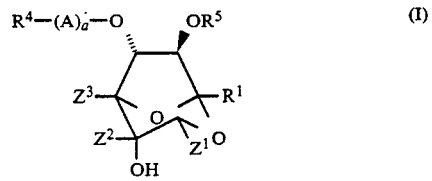

14 Claims, No Drawings

CHOLESTEROL LOWERING COMPOUNDS

This application is a continuation-in-part of co-pending U.S. application Ser. No. 07/935,485 filed Aug. 25, 1992 now abandoned.

BACKGROUND OF THE INVENTION

Hypercholesterolemia is known to be one of the prime risk factors for ischemic cardiovascular disease, such as arteriosclerosis. Bile acid sequestrants have been use to treat this condition; they seem to be moderately effective but they must be consumed in large quantities, i.e. several grams at a time and they are not very palatable.

MEVACOR ® (lovastatin), and Zocor ® (simvastatin) now commercially available, are members of a group of very active antihypercholesterolemic agents that function by limiting cholesterol biosynthesis by inhibiting the enzyme, HMG-CoA reductase.

Squalene synthase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analogs containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthase.

Recently certain nonphosphorous containing inhibitors of squalene synthase have been isolated as natural products. These natural product inhibitors are described in U.S. Pat. Nos. 5,102,907; 5,096,923; 5,055,487 and 5,026,554. Semisynthetic derivatives of these natural products have been described in EPO 512,865, which published on Nov. 11, 1992, the contents of which are incorporated by reference. A need still remains for a more effective squalene synthetase inhibitor, i.e. one that provides a greater antihypercholesterolemic effect and exhibits a good safety profile.

DETAILED DESCRIPTION OF THE INVENTION

This invention relates to compounds of structural formula (I):

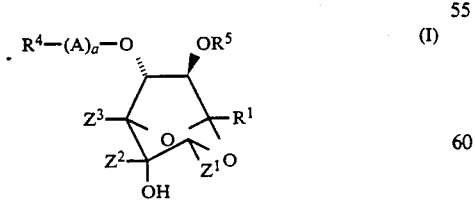

wherein
A is —C(O)—, —NR$^3$—C(O)—, or —OC(O)—;
a is zero or 1;
R$^1$ is selected from the group consisting of:
(1) C$_{1-20}$alkyl, (2) substituted C$_{1-20}$alkyl in which one or more substituents is selected from a group herein termed X$^3$ wherein the group X$^3$ consists of:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$, wherein aryl is substituted with X and Y,
(m) R$^3$—C(O)—NR$^3$—,
(n) R$^3$R$^3$N—C(O)—,
(o) —CO$_2$H,
(p) —vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O— or —S(O)$_n$— and wherein one or more carbon substituents is selected from the group X$^3$, defined above;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the carbons is substituted with a substituent selected from the group X$^3$, defined above;
(9) C$_{2-20}$alkenyl wherein alkenyl contains one or more double bonds and one or more of the nonolefinic carbons is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more of the carbons is substituted with a substituent selected from the group X$^3$, defined above;
(11) C$_{3-10}$cycloalkyl;
(12) substituted C$_{3-10}$cycloalkyl in which one or more of the substituents is selected from the group consisting of C$_{1-10}$alkyl—S(O)$_n$—, C$_{1-10}$alkyl, and the members of the group X$^3$, defined above;
each R$^2$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl— wherein heteroaryl is substituted with X and Y;
(6) heterocycloalkylC$_{1-4}$alkyl—;
(7) C$_{2-10}$alkenyl;

(8) arylC$_{2-10}$alkenyl wherein aryl is substituted with X and Y; and
(9) C$_{3-10}$alkynyl;

each R$^3$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl— wherein heteroaryl is substituted with X and Y;
(6) heterocycloalkylC$_{1-4}$alkyl—;
(7) C$_{2-10}$alkenyl;
(8) arylC$_{2-10}$alkenyl wherein aryl is substituted with X and Y;
(9) C$_{3-10}$alkynyl;
(10) hydrogen; and
(11) C$_{1-5}$alkyl substituted with X$^1$;

R$^4$ is selected from the group consisting of:
(1) C$_{1-20}$alkyl;
(2) substituted C$_{1-20}$alkyl in which one or more substituents is selected from the group X$^3$, defined above;
(3) C$_{1-20}$alkyl wherein one or more of the carbons is replaced by —NR$_3$—, —O—, or —S(O)$_n$—;
(4) substituted C$_{1-20}$alkyl wherein one or more of the carbons is replaced by —NR$^3$—, —O— or —S(O)$_n$— and wherein one or more carbon substituents is selected from the group X$^3$, defined above;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the carbons is substituted with a substituent selected from the group X$^3$, defined above.
(9) C$_{2-20}$alkenyl wherein alkenyl contains one or more double bonds and one or more of the nonolefinic carbons is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more of the carbons is substituted with a substituent selected from the group X$^3$, defined above;
(11) C$_{3-10}$cycloalkyl;
(12) substituted C$_{3-10}$cycloalkyl in which one or more of the substituents is selected from the group X$^3$, defined above;
(13) hydrogen;

R$^5$ is selected from the group consisting of:
(1) hydrogen;
(2) C$_{1-10}$alkyl;
(3) aryl substituted with X and Y;
(4) arylC$_{1-4}$alkyl, wherein aryl is substituted with X and Y;
(5) R$^2$O—C(O)—;
(6) C$_{3-10}$cycloalkyl;
(7) R$^3$—C(O)—; and
(8) R$^3$R$^3$N—C(O)—;

n is zero, 1 or 2;
Z$^1$ is selected from:
(1) —CH$_3$,
(2) —CO$_2$R$^6$,
(3) —COSR$^6$,
(4) —CONHR$^6$,
(5) —CONHOH,
(6) —CONHSO$_2$R,
(7) tetrazolyl and
(8) —H;

Z$^2$ is —CO$_2$R$^6$;

Z$^3$ is selected from:
(1) —CO$_2$R$^6$,
(2) —COSR$^6$,
(3) —CONHR$^6$,
(4) —CONHOH,
(5) —CONHSO$_2$R, and
(6) tetrazolyl;

R is selected from:
(1) C$_{1-10}$alkyl,
(2) phenyl substituted with X and Y,
(3) C$_{1-10}$alkyl substituted with phenyl, wherein the phenyl is substituted with X and Y, and
(4) heteroaryl substituted with X and Y;

R$^6$ is independently selected at each occurrence from the group consisting of:
(1) C$_{1-20}$alkyl;
(2) substituted C$_{1-20}$alkyl in which one or more substituents is selected from the group X$^3$, defined above,
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O—, or —S(O)$_n$— and wherein one or more carbon substituents is selected from the group X$^3$, defined above;
(5) C$_{2-20}$alkenyl wherein alkenyl contains one or more double bonds;
(6) substituted C$_{2-20}$alkenyl wherein alkenyl contains one or more double bonds and wherein one or more of the carbons is substituted with a substituent selected from the group X$^3$, defined above;
(7) C$_{2-20}$alkenyl wherein alkenyl contains one or more double bonds and one or more of the nonolefinic carbons is replaced by —NR$^3$—, —O—, or —S(O)$_n$—;
(8) substituted C$_{2-20}$alkenyl wherein alkenyl contains one or more double bonds and one or more of the nonolefinic carbons is replaced by —NR$^3$—, —O—, or —S(O)$_n$— and wherein one or more of the carbons is substituted with a substituent selected from the group X$^3$, defined above;
(9) C$_{2-20}$alkynyl wherein alkynyl contains one or more triple bonds;
(10) substituted C$_{2-20}$alkynyl wherein alkynyl contains one or more triple bonds and wherein one or more of the carbons is substituted with a substituent selected from the group X$^3$, defined above;
(11) C$_{2-20}$alkynyl wherein alkynyl contains one or more triple bonds and one or more of the saturated carbons is replaced by —NR$^3$—, —O—, or —S(O)$_n$—;
(12) substituted C$_{2-20}$alkynyl wherein alkynyl contains one or more triple bonds and one or more of the saturated carbons is replaced by —NR$^3$—, —O—, or —S(O)$_n$— and wherein one or more of the carbons is substituted with a substituent selected from the group $X^3$, defined above;

(13) aryl substituted with X and Y;

(14) heteroaryl substituted with X and Y;

(15) $C_{3-5}$cycloalkyl;

(16) substituted $C_{3-5}$cycloalkyl in which one or more of the substituents is selected from:

(a) $R^3O—$, and (b) $R^3R^3N—$; and

(17) hydrogen;

aryl including X, Y substitution is:

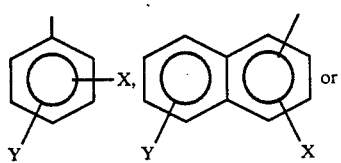

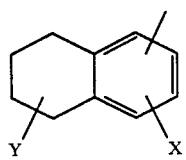

heteroaryl including X, Y substitution is selected from

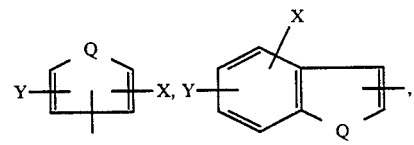

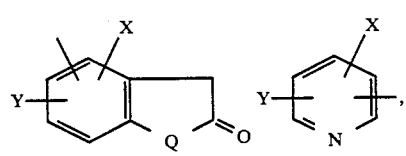

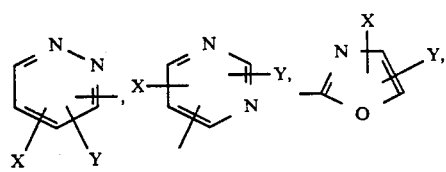

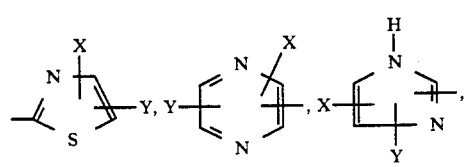

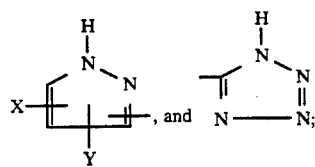

wherein:

Q is $—NR^3$, $—O—$ or $—S—$;

heterocycloalkyl is selected from:

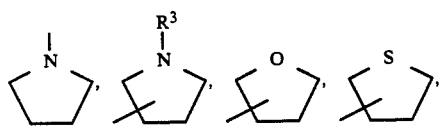

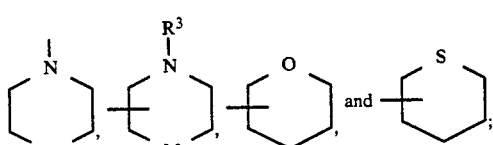

wherein:

M is $—NR^3$, $—O—$, $—S—$ or $—CH_2—$

X and Y are each independently selected from:

(1) hydrogen;

(2) hydroxy;

(3) halogen;

(4) trifluoromethyl;

(5) $C_{1-10}$alkyl;

(6) aryl substituted with $X^1$ and $Y^1$;

(7) $R^2O—$;

(8) arylcarbonyloxy-, wherein aryl is substituted with $X^1$ and $Y^1$;

(9) $R^3—C(O)—O—$;

(10) $—CO_2R^2$;

(11) $—CO_2H$; and

(12) nitro; and $X^1$ and $Y^1$ are each independently selected from:

(1) hydrogen;

(2) hydroxy;

(3) halogen;

(4) trifluoromethyl;

(5) $C_{1-4}$alkyl;

(6) $R^2O—$;

(7) $R^3—C(O)—O—$;

(8) $—CO_2R^2$;

(9) $—CO_2H$; and

(10) nitro;

provided that one and only one of $Z^1$ and $Z^3$ must be selected from the group consisting of $—CONHSO_2R$, $—CONHOH$ and tetrazolyl;

and the pharmaceutically acceptable salts thereof.

In one embodiment of this invention are the compounds of formula I having a structural formula selected from

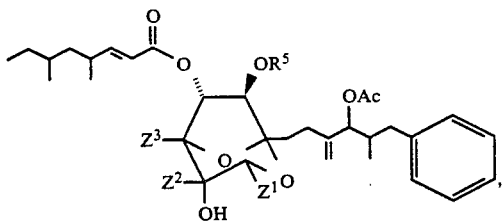

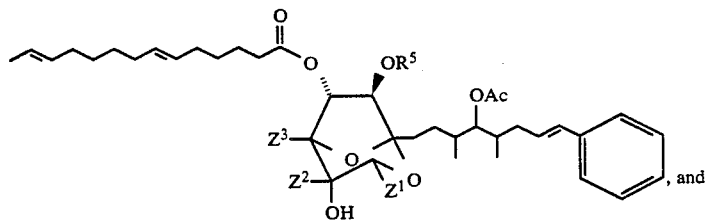, and

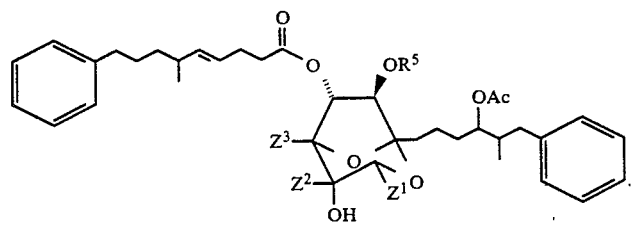

A second embodiment of this invention is further limited to compounds having the structural formula

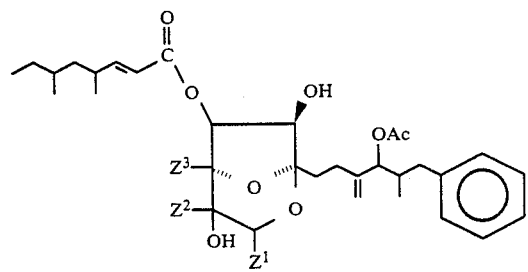

IA wherein
$Z^1$ is selected from the group consisting of
  (a) —CONHSO$_2$R and
  (b) —CONHOH;
R is selected from the group consisting of
  (a) $C_{1-10}$ alkyl,
  (b) phenyl substituted with X and Y, and
  (c) heteroaryl substituted with X and Y;
X and Y are each independently selected from
  (a) hydrogen,
  (b) $C_{1-5}$ alkyl,
  (c) —CO$_2$H,
  (d) $C_{1-5}$ alkoxy,
  (e) nitro,
  (f) halogen, and
  (g) —S(O)$_n$ $C_{1-5}$alkyl, n=0, 1, 2;
$Z^2$ and $Z^3$ are each —CO$_2$R$^6$; and
$R^6$ is independently selected at each occurrence from
  (a) H,
  (b) $C_{1-5}$ alkyl, and
  (c) $C_{1-5}$ alkyl substituted with a member of the group consisting of
    (i) phenyl,
    (ii) phenyl substituted with methyl, methoxy, halogen (Cl, Br, I, F) or hydroxy, and
    (iii) $C_{1-5}$ alkylcarbonyloxy.

A third embodiment is still further limited to compounds wherein $Z^1$ is —CONHSO$_2$R or —CONHOH, R is methyl or phenyl, and X and Y are independently selected from hydrogen and halogen.

A fourth embodiment is still further limited to compounds wherein $R^6$ is independently selected at each occurrence from
  (a) hydrogen,
  (b) $C_{1-5}$ alkyl, and
  (c) $C_{1-5}$ alkyl substituted with $C_{1-5}$ alkyl carbonyloxy.

Within the fourth embodiment is one class of compounds wherein $R^6$ is hydrogen at each occurrence. Exemplifying this class are the compounds wherein
  (1) $Z^1$ is —CONHSO$_2$R and R is
    (a) methyl,
    (b) phenyl or
    (c) 4-chlorophenyl; or
  (2) $Z^1$ is —CONHOH.

In a second class within the fourth embodiment are compounds wherein at least one of $R^6$ is —CH$_2$OC-(O)C(CH$_3$)$_3$. Exemplifying this class are the compounds wherein $Z^1$ is —CONHSO$_2$R, $Z^2$ is —COOCH$_2$OC-(O)C(CH$_3$)$_3$, $Z^3$ is —COOH, and R is
  (a) methyl or
  (b) phenyl.

Except where specifically defined to the contrary, the word "alkyl" includes both branched and straight chain saturated aliphatic hydrocarbon groups having the specified number of carbon atoms, such as e.g., methyl (Me), ethyl (Et), iso-propyl (i-Pr), and tert-butyl (t-Bu). Acyl, i.e. —COCH$_3$, is abbreviated herein as "Ac", phenyl is "Ph", benzyl is "Bn", and ethyl acetate is "EtOAc." Halogen is defined as —Cl, —Br, —I and —F.

SCHEME 1
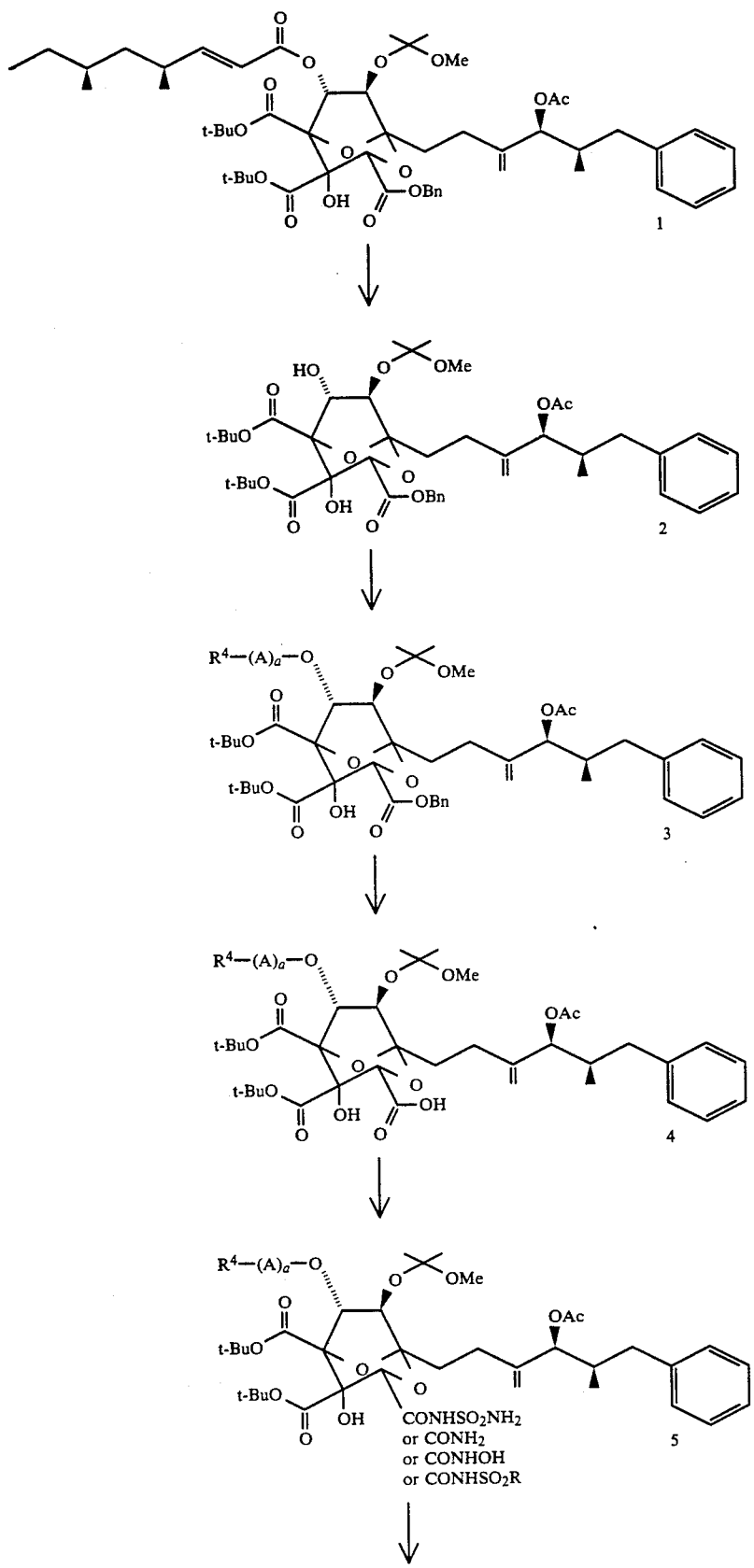

SCHEME 1
-continued
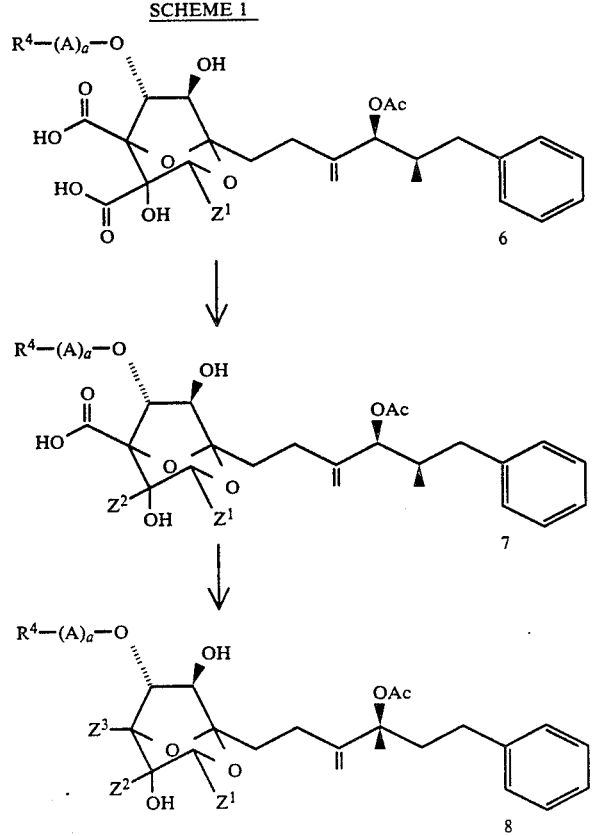

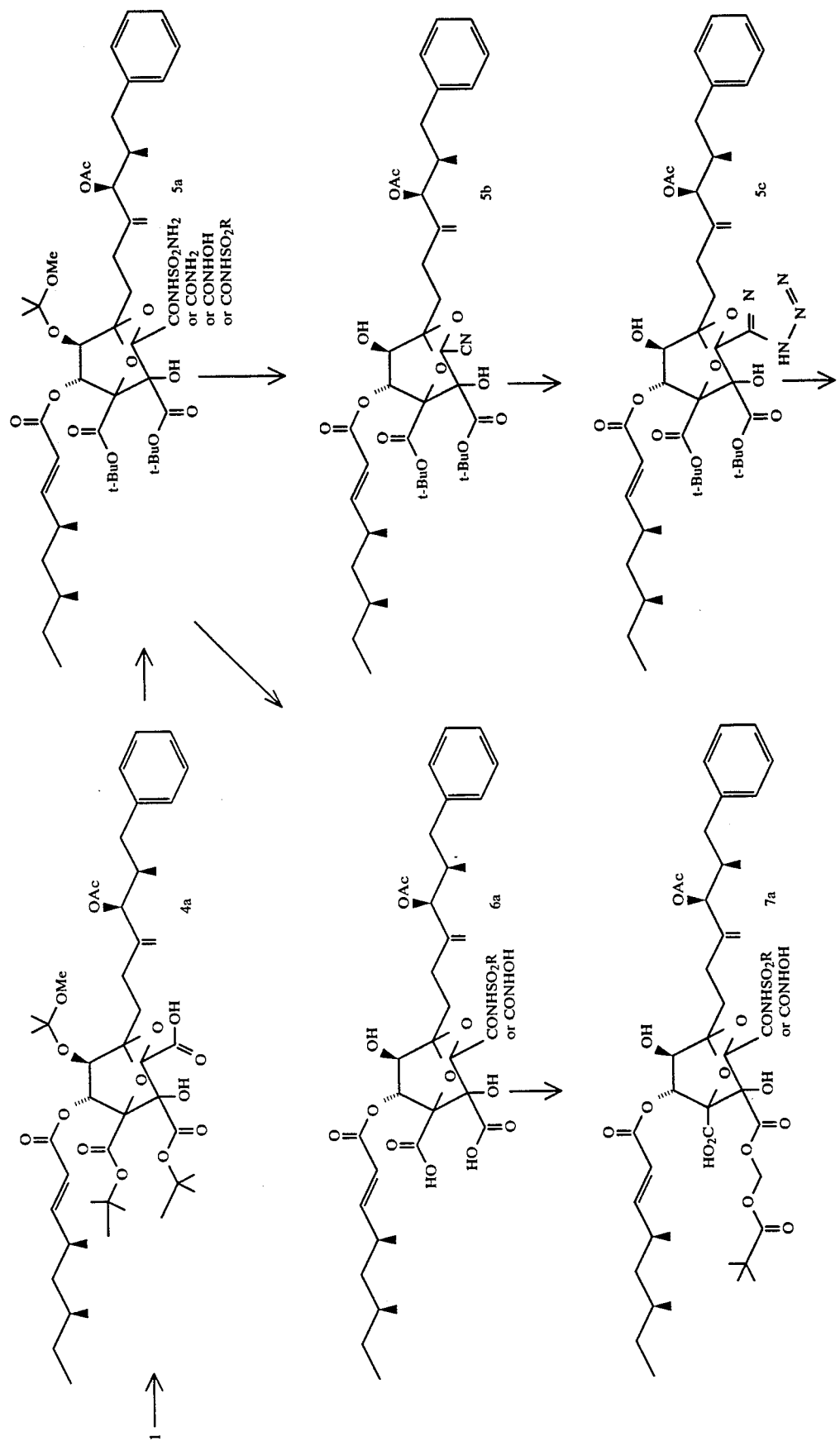

-continued
SCHEME 2
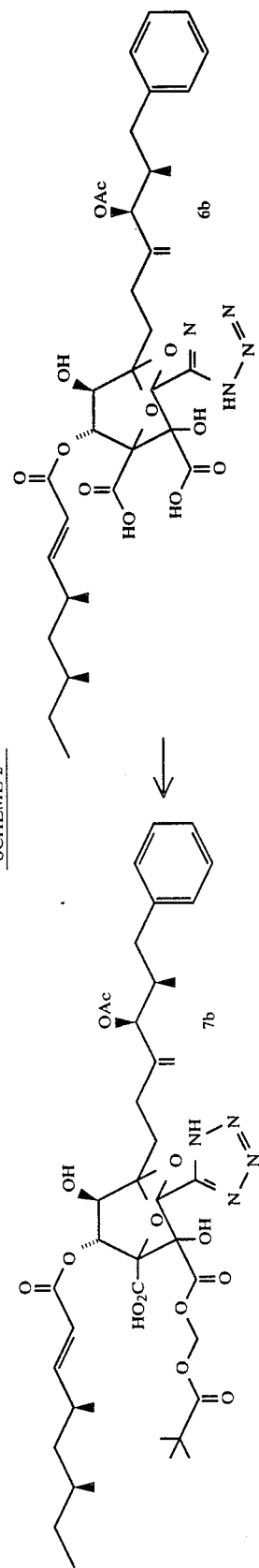

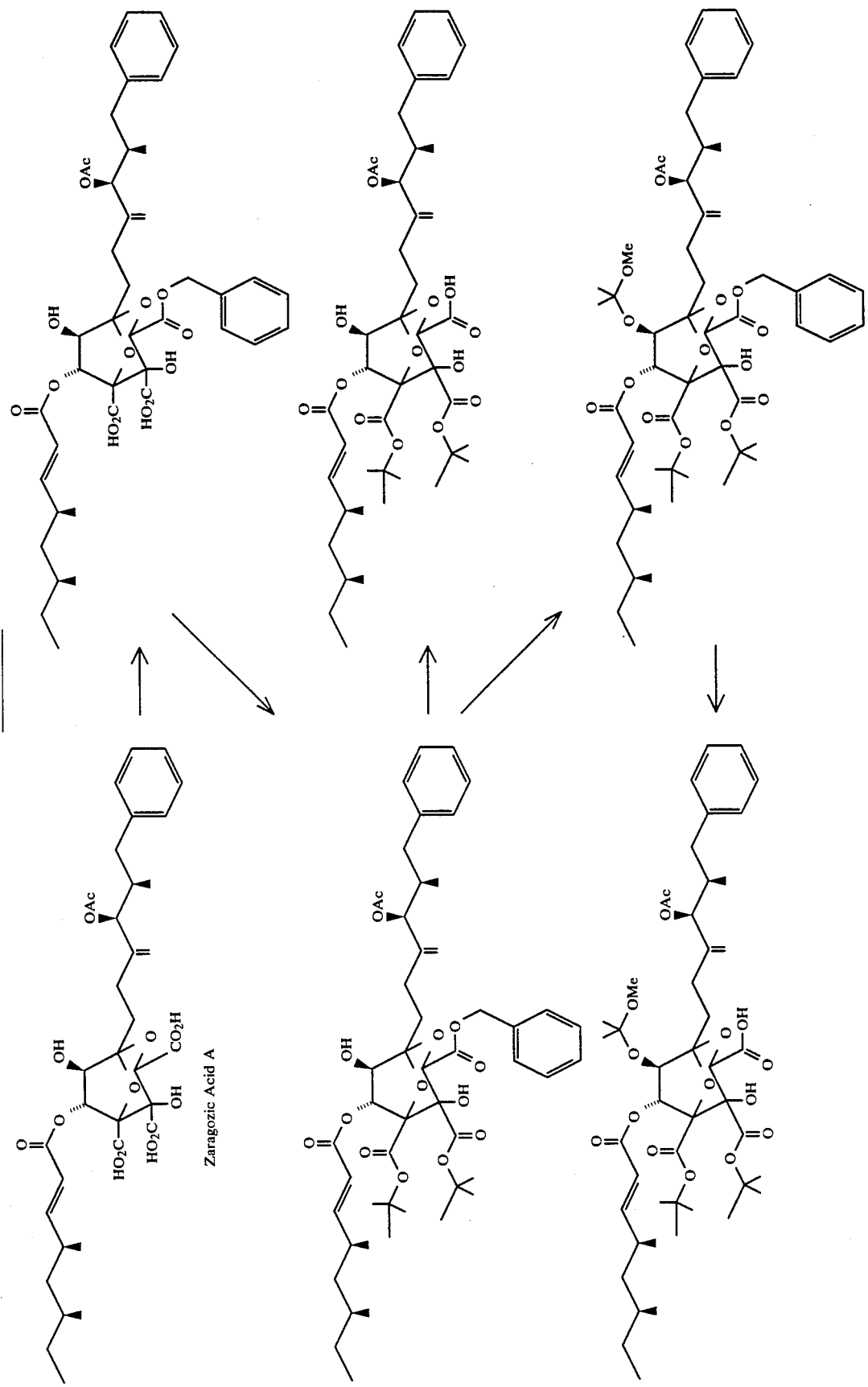
SCHEME 3

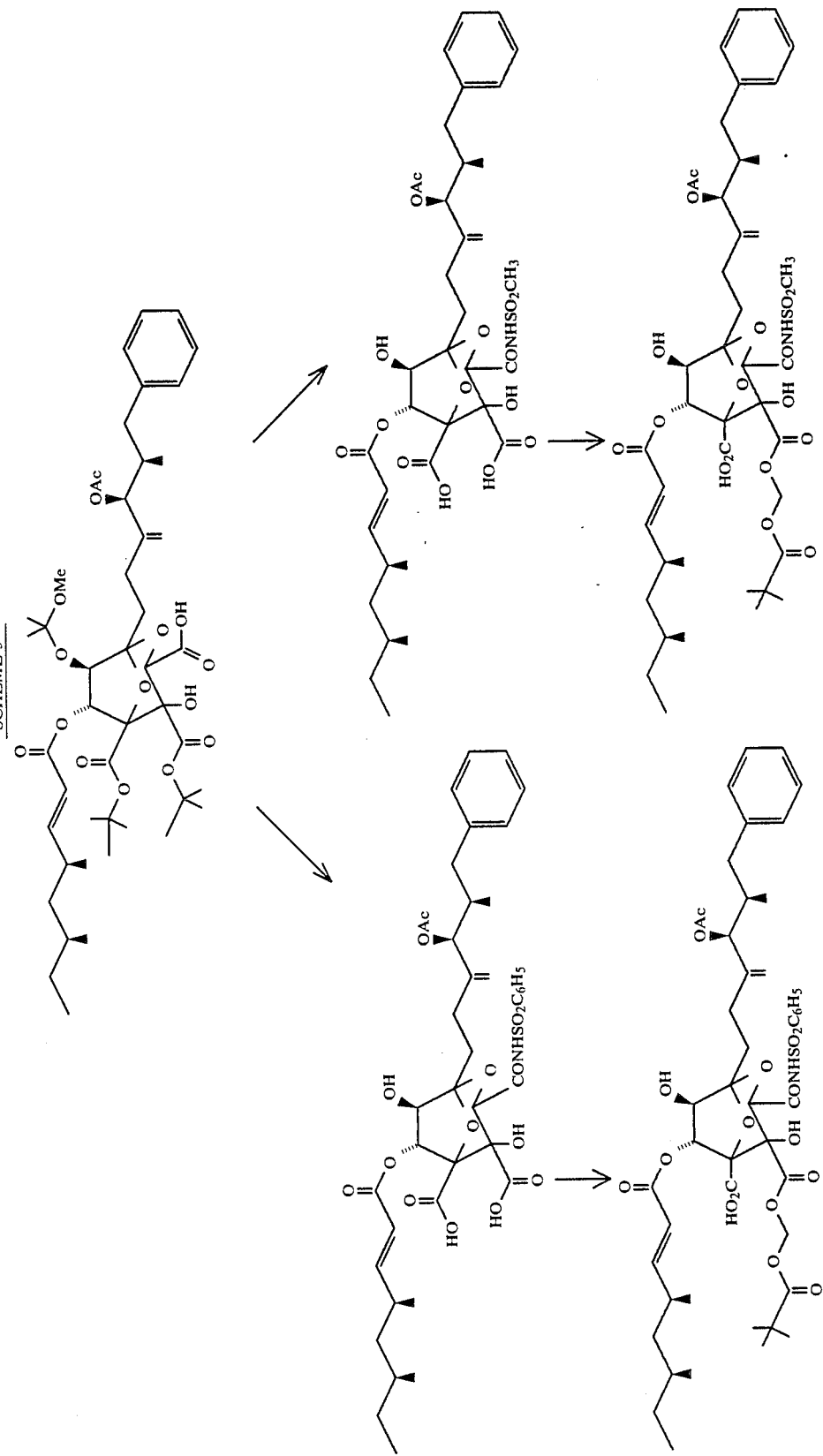
-continued
SCHEME 3

SCHEME 4
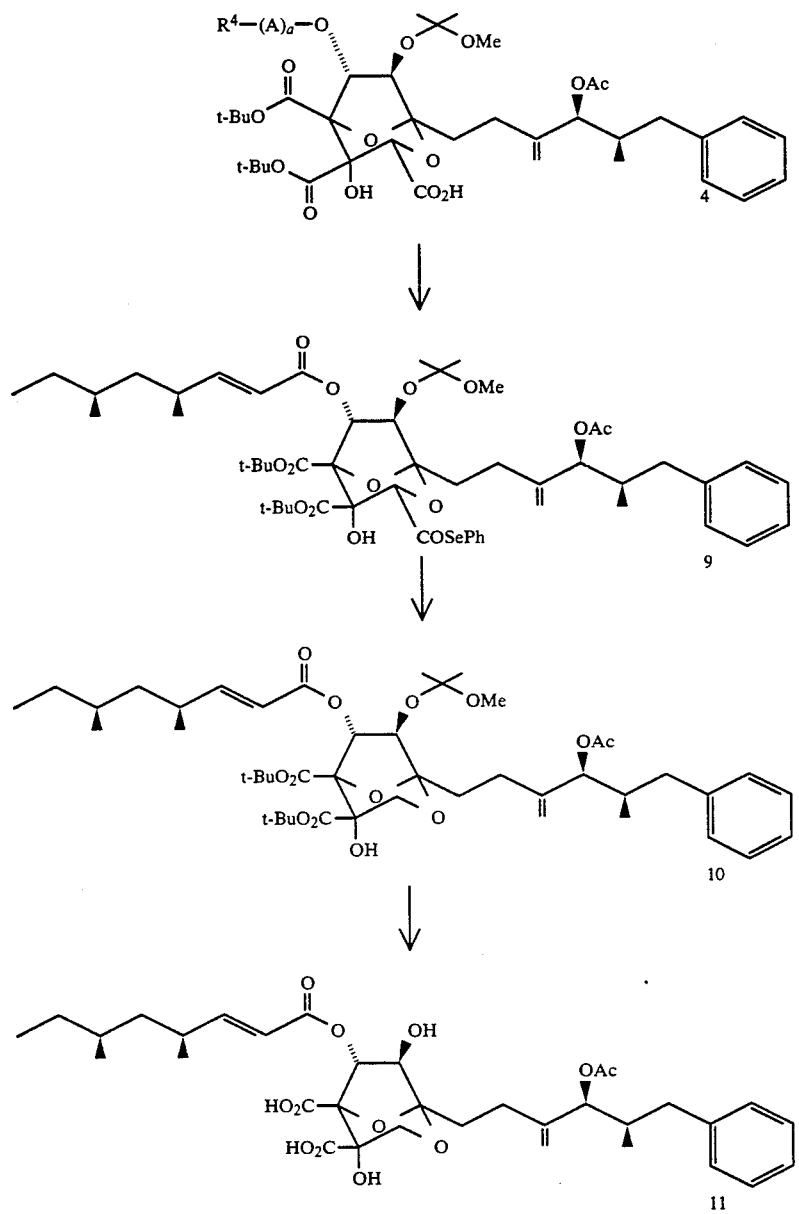
SCHEME 5
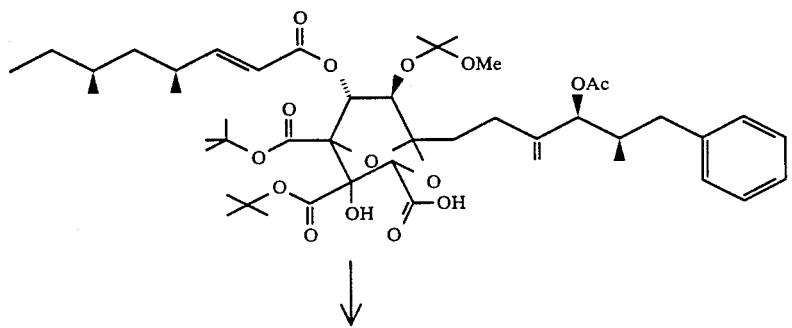

SCHEME 5

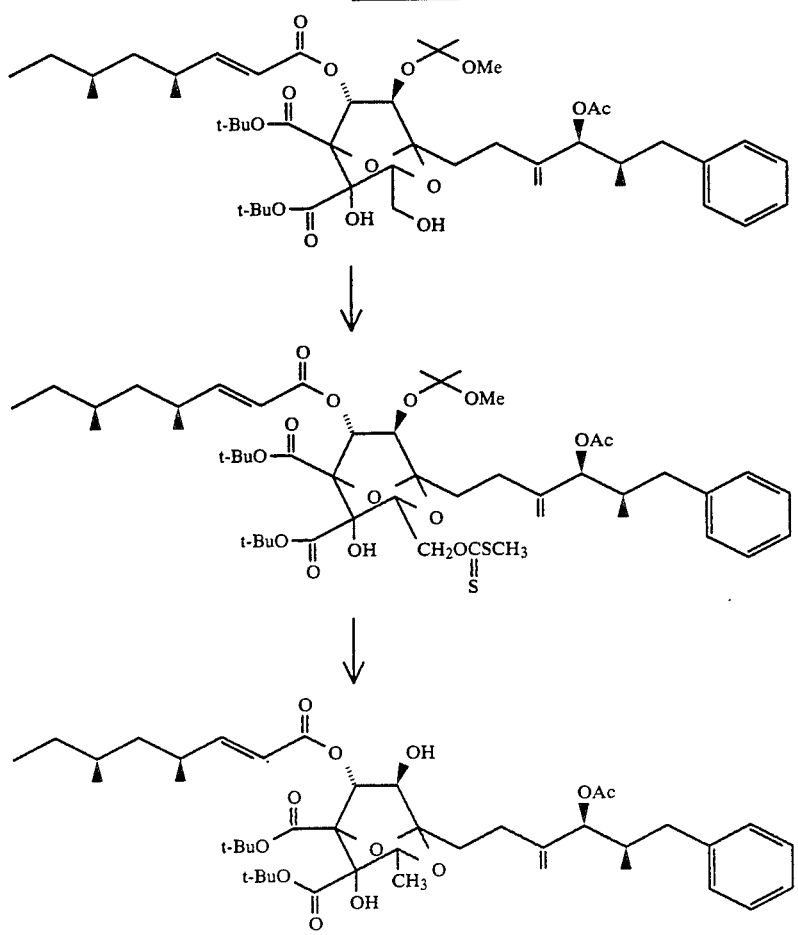

40

The compounds of the present invention may be prepared following the methodologies described in Schemes 1 through 5 starting from Zaragozic acid A ("A"), Zaragozic acid B ("B") or Zaragozic acid C ("C"). Although compound A and its derivatives are shown at certain points in the schemes, the methodology of Schemes 1 through 4 can be employed starting with compounds B and C as well. Compound A is the first structure shown in Scheme 3. Compounds B and C are depicted below. The preparation of the starting materials A, B, and C, is described in U.S. Pat. Nos. 5,096,923; 5,055,487; and 5,102,907; respectively.

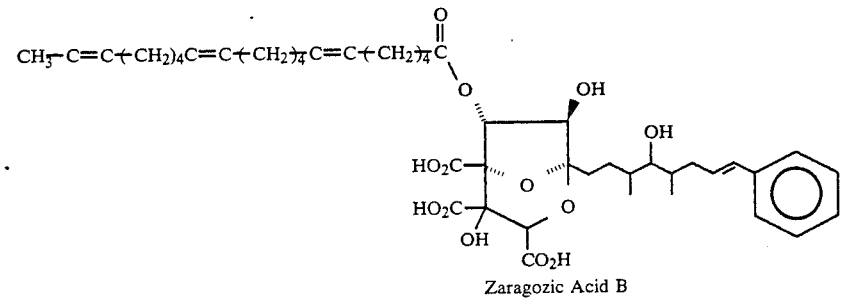

Zaragozic Acid B

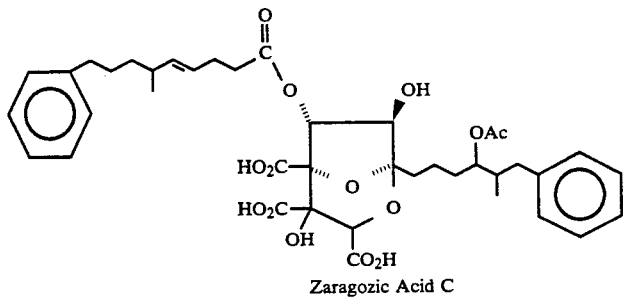
Zaragozic Acid C

The following general procedures are shown in Schemes 1 and 2.

C6 MODIFICATION

"A"-3-benzyl-4,5-di-t-butyl triester 1 was made as shown in EP 0 512 865 A2 and as shown in Scheme 3, described below. This intermediate could be modified at C6 by first removing the C6 acyl side chain with $NH_2OH$/NaOAc in methanol. The resulting C6 alcohol 2 could be converted to 3 esters, carbamates or ethers by standard procedures such as carbonyl diimidazole followed by an alcohol, carbonyl diimidazole followed by an amine or a base such as NaH followed by alkyl halides respectively. The C6 alcohol 2 can be converted to 3 carbonates as described in EPO 512 865.

C3 MODIFICATION

Esters and thioesters at C3 could be prepared from 4 or 4a as shown in EP 0 512 865.

Acyl sulfonamides, carboxamic acids and amides at C3 position could be prepared from 1 or 3 by first removing the benzyl group with Pd-C/methyl cyclohexadiene to form 4 or 4a respectively, conversion of the resulting acid to mixed anhydride, acyl imidazolide or acyl halides with reagents such as isobutyl chloroformate, carbonyl diimidazole or thionyl chloride and finally treatment of the acyl halide, acyl imidazolide or mixed anhydride with sulfonamides to form acyl sulfonamides, hydroxylamine to form hydroxamic acids or ammonia to form carboxamides 5 or 5a.

The C3 amide 5 or 5a obtained above could be treated with a base followed by appropriately substituted sulfonyl chloride to form acyl sulfonamides, or it could also be treated with a dehydrating agent to form a C3 nitrile 5b which could be converted to tetrazolyl 5c upon treatment with azides such as sodium azide.

C4 MODIFICATION

The t-butyl protecting groups of compounds 5 shown above could be removed by stirring with trifluoroacetic acid in methylene chloride. The resulting C4 di-acids 6 could then be esterified as shown in EP 0 512 865 A2 to yield compounds 7.

C5 MODIFICATION

Compounds 7 with free C5 carboxylic acid groups could be modified as shown above for C3 groups.

C1 MODIFICATION

Sidechains at the C1 position can be prepared from Zaragozic acid A, B or C as shown in EP 0 512 865.

C7 MODIFICATION

Ethers at the C7 position can be prepared from compound 2 as shown in EP 0 512 865.

As detailed in Scheme 3, the 3-carboxy moiety of zaragozic acid is selectively esterified to form for example the benzyl ester followed by blocking the C4 and C5 carboxyl groups using O-t-butyl-N-N'-disopropyl isourea followed by protection of the 7-hydroxy with a methyl-1-methoxy-ethyl ether moiety (MME) and then selective removal of the 3-benzyl ester to yield the 7-MME-4,5-di-t-butyl ester of zaragozic acid A. This is followed by the formation of the appropriate alkyl or aryl sulfonamide. The 4,5-t-butyl blocking groups and the 7-MME blocking group are then removed under standard conditions. The C4 and C5 carboxy groups may be esterified with the appropriate alkylating agent and DBU. Esterification may lead to a mixture of mono and diesters and these may be readily separated, by preparative HPLC using a C-8 reverse phase column and a gradient solvent of $H_2O$/acetonitrile.

To make C3 decarboxylated compounds, the methodology of Scheme 4 is followed. The 3-phenylseleno ester of 4 is formed and then the seleno ester moiety is removed employing tributyl tin hydride, to yield the 3-descarboxy compound 10. The 4,5-t-butyl and 7-hydroxy blocking groups are then removed under standard conditions to yield 11.

To make C3-methyl compounds, the methodology of Scheme 5 is followed. For example, the 3-COOH group is reduced to hydroxymethyl, and then the primary alcohol is converted to xanthate. Deoxygenation of the xanthate with tributyltin hydride yields a C3-methyl compound.

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthase which comprises the administration to a subject in need of such treatment a nontoxic therapeutically effective amount of compound represented by structural formula (I) and pharmaceutically acceptable salts thereof. Specifically, the compounds of this invention are useful in treating disease conditions such as, but not limited to, hypercholesterolemia which result from the action of the enzyme squalene synthase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N-N'-dibenzylethylendiamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one or two of the carboxyl groups are in the salt form.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-COA synthase inhibitors, and squalene expoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Appropriate daily dosages for adults are niacin (2-8 gm), probucol (up to 1000 mg), clofibrate (up to 2 gm) and gemfibrozil (800-1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic squalene synthase inhibitory activity of representative compounds of this invention was measured by the standard in vitro protocol described below:

PREPARATION OF MICROSOMES

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthase activity in these aliquots is stable for at least several months.

PARTIAL PURIFICATION OF PRENYL TRANSFERASE

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 $\mu$mole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 $\mu$M leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5 with 6N HOAc and centrifuged at 100,000×g for 1 hour. This supernatant was adjusted to pH 7.0 with 3N KOH and a 35–60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM $\beta$-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

ENZYMATIC SYNTHESIS OF [4-$^{14}$C]FARNESYL-PYROPHOSPHATE

The solvent (ethanol: 0.15N NH$_4$OH, 1:1) was removed from 55 $\mu$Ci of [4-$^{14}$C]isopentenyl pyrophosphate(47.9 $\mu$Ci/$\mu$mole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 $\mu$l of a 20 mM solution, and 50 $\mu$l of the ammonium sulfate suspension of prenyl transferase were added to initiate the reaction. This incubation contained 5 $\mu$moles of geranyl pyrophosphate, 1.15 $\mu$moles of isopentenyl pyrophosphate, 6 $\mu$moles of MgCl$_2$ of 0.18 units of prenyl transferase in a volume of 900 $\mu$l. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5. The yield was 50.7 µCi (92%) of [4-$^{14}$C]farnesyl pyrophosphate. The [4-$^{14}$C]farnesyl pyrophosphate was stored in 5 aliquots at −70° C.

SQUALENE SYNTHASE ASSAY

Reactions were performed in 16×125 mm screw cap test tubes. A batch assay mix was prepared from the following solution:

| | µl per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 µCi/µmole, and 0.025 µCi/3.0 µl | 3.0 | 150 |
| 7. H$_2$O | 24 | 1200 |

This assay mix was degassed under a vacuum and flushed with N$_2$. Solutions of the squalene synthase inhibitors were prepared either in DMSO or MeOH and a 1:120 dilution of the microsomal protein was made with the original homogenizing buffer. For each reaction, 87 µl of the assay mix was taken with 3 µl of an inhibitor solution (DMSO or MeOH in the controls), warmed to 30° C. in a water bath and then the reaction was initiated by the addition of 10 µl of the 1:120 dilution of microsomal protein (0.6 µg protein total in the assay). The reactions were stopped after 20 minutes by the addition of 100 µl of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that gives 50% inhibition as determined from these plots.

Representative compounds of this invention exhibited IC$_{50}$ values which were all <500 µM.

EXAMPLE 1

Preparation of the 3-benzyl ester of Zaragozic Acid A (Compound of formula IA wherein Z$^1$ is COO-Benzyl; Z$^2$=Z$^3$=—COOH)

Acetyl chloride (0.4 mL) was added to benzyl alcohol (10 mL) and the reaction mixture stirred at room temperature for 30 min. Zaragozic Acid A ("A") was added and the reaction mixture stirred for additional six hours. The mixture was degassed, poured into acetonitrile-water mixture (200 mL, 38%), filtered through a bed of C-8 reverse phase column (30 g. Baker) to remove unreacted benzyl alcohol, washed several times with acetonitrile (400 mL). Evaporation under vacuum gave the titled compound (1) (86% pure by HPLC). Further purification was carried out by reverse phase chromatography (C-8 Baker, 58% acetonitrile in water).

$^1$H NMR (300 MHz, CD$_3$OD) δ7.46–7.12 (m, 10H), 6.88 (dd, J=8.9, 18 Hz, 1H), 6.38 (brs, 1H), 5.48 (d, J=15 Hz, 1H), 5.42 (s, 1H), 5.23 (dd, J=14, 5.1 Hz, 2H), 5.14 (s, 1H), 5.04 and 5.00 (2s, 2H), 4.06 (brs, 1H), 2.71 (m, 1H), 2.54–2.00 (m, 7H), 2.12 (s, 3H), 1.50–1.1 (m, 6H), 1.07 (d, J=6 Hz, 3H), 0.90 (m, 9H); FAB m/e 793 (M+2 Li), 799 (M+3 Li).

EXAMPLE 2

Compound of formula IA wherein Z$^1$ is COO-Benzyl; Z$^2$=Z$^3$=COOC(CH$_3$)$_3$ A solution of "A"-3-benzyl ester (from Example 1) (100 mg) dissolved in methylene chloride (2 mL) was treated with O-t-butyl-N,N′-diisopropylisourea (300 mg) and heated at 40° C. for 2 days. The reaction mixture was cooled to room temperature, concentrated and filtered through a bed of silica (25% ethyl acetate in hexane) to yield pure "A"-3-benzy-4,5-di-t-butyl-ester (2).

$^1$NMR (400 MHz, CDCl$_3$) δ7.35–7.08 (m, 10H), 6.88 (dd, J=8.4, 16 Hz, 1H), 5.97 (d, J=1 Hz, 1H), 5.75 (d, J=16 Hz), 1H), 5.42 (s, 1H), 5.16 (dd, J=12, 6.4 Hz, 2H), 5.06 (br s, 1H), 4.94 (br s, 2H), 4.00 (br s, 1H), 2.96 (d, J=2 Hz, 1H), 2.66 (m, 1H), 2.5–2.2 (m, 5H).

EXAMPLE 3

"A"-7-(1-methyl-1-methoxyethyl ether)-3-benzyl-4,5-di-t-butyl ester

A solution of "A"-3-benzyl-4,5-di-t-butyl ester (from Example 2) (3.69 g) and 2-methoxypropene (4.1 mL) in methylene chloride (43 mL) was cooled to 0° and pyridinium p-toluenesulfonate (58.5 mg) was added. After stirring for 2 hr the solution was neutralized with saturated sodium bicarbonate and extracted with diethyl ether. The organic layer was separated and washed with brine, dried over magnesium sulfate, filtered and the filtrate evaporated in vacuo. Purification of the residue by flash column (silica gel, ethyl acetate/hexane 1:4) gave the ketal (3).

$^1$NMR (400 MHz, CD$_3$OD) δ7.4–7.12 (m, 10H), 6.88 (dd, J=8.5, 15.6 Hz, 1H), 6.48 (d, J=1.85 Hz, 1H), 5.84 (d, J=15.6 Hz, 1H), 5.29 (s, 1H), 5.23 and 5.10 (each d, J=12 Hz, each 1H), 5.07 (d, J=4.8 Hz, 1H), 4.99 and 4.99 (each s, each 1H), 4.23 (d, J=1.85 Hz, 1H), 3.18 (s, 3H), 2.09 (s, 3H), 1.52 and 1.39 (each s, each 9H), 1.34 (s), 1.26 (s), 1.02 (d, J=6.7 Hz, 3H), 0.9–0.8 (m, 9H).

EXAMPLE 4

Preparation of "A"-7-(1-methyl-1-methoxy ethylether)-4,5-di-t-butyl ester

To a solution of the product of Example 3 (100 mg) in methanol (4 mL) was added methyl cyclohexadiene (200 µL) and Pd/c (50 mg). The reaction mixture was stirred at 30°–35° C. for 1.5 hours and filtered over celite. The filtrate was evaporated under vacuum to give the titled compound (4).

$^1$H NMR (200 MHz, CD$_3$OD) δ7.3–7.15 (m, 5H), 6.92 (dd, J=8.4, 15.6 Hz, 1H), 6.50 (d, J=1.7 Hz, 1H), 5.85 (d, J=15.6 Hz, 1H), 5.19 (s, 1H), 5.08 (d, J=4.78 Hz, 1H), 5.02 and 4.97 (each bs, each 1H), 4.25 (d, J=1.7

Hz, 1H), 3.19 (s, 3H), 2.10 (s, 3H), 1.63 and 1.40 (each s, each 9H), 1.35 (j), 1.26 (d, J=5.8 Hz, 3H), 1.02 (d, J=6.73 Hz, 3H), 0.89–0.82 (m, 9H).

EXAMPLE 5

Preparation of Zaragozic Acid A-3-methylsulfonamide (Compound of formula IA wherein $Z^1$ is CONH-SO$_2$Me; $Z^2=Z^3=$—COOH)

175 mg of the product of Example 4 in 2 ml methylene chloride was treated with 26 μL of N-methyl morpholine and stirred for 10 minutes at room temperature. The solution was cooled to −30° C. and then treated with 32 μL of isobutyl chloroformate. Stirring was continued for 20 minutes and then a solution of 28.5 mg of methylsulfonamide and 90 μL DBU in 2.5 mL tetrahydrofuran was added and stirred for 30 minutes and warmed up to ambient temperature. The solution was evaporated, redissolved in 10 mL of ethyl acetate, washed with 3×20 mL of 1N HCl and the organic layer was separated, dried over sodium sulfate and evaporated. Purification by filtering over silica gave "A"-3-methylsulfonamide-7-MME-4,5-di-t-butyl ester.

$^1$H NMR (CD$_3$OD, 400 MHz) δ7.3–7.15 (m, 5H), 6.84 (dd, J=15.64, 9, Hz 1H), 6.39 (d, J=1.84 Hz, 1H), 5.81 (dd, J=15.64, 1.0 Hz, 1H), 5.29 (s, 1H), 5.07 (d, J=4.64 Hz, 1H), 5.05 and 5.00 (ea s, ea 1H), 4.13 (d, J=1.84 Hz, 1H), 3.24 (s, 3H), 2.6–2.15 (m, 5H), 2.10 (s, 3H), 1.62 and 1.41 (ea s, ea 9H), 1.4–1.1 (m, 5H), 1.02 (d, 7 Hz, 3H), 0.88 (m, 9H).

The above diester was dissolved in 1.5 mL of methylene chloride and 0.5 mL trifluoroacetic acid and stirred overnight at room temperature. Evaporation gave the titled compound.

$^1$H NMR (CD$_3$OD, 400 MHz) δ7.3–7.12 (m, 5H), 6.84 (dd, J=15.7, 9, Hz 1H), 6.26 (d, J=1.88 Hz, 1H), 5.78 (dd, J=15.7, 0.88 Hz, 1H), 5.25 (s, 1H), 5.07 (d, J=4.56 Hz, 1H), 5.05 and 5.00 (ea s, ea 1H), 4.08 (d, J=1.6 Hz, 1H), 3.25 (s, 3H), 2.6–2.15 (m, 5H), 2.10 (s, 3H), 1.4–1.1 (m, 5H), 1.02 (d, 7 Hz, 3H), 0.88 (m, 9H).

EXAMPLE 6

Preparation of Zaragozic Acid A-3-methyl sulfonamide-4-methyl-pivalate (Compound of formula IA wherein $Z^1$ is CONHSO$_2$Me; $Z^2$ is —COOCH$_2$OC(O)C(CH$_3$)$_3$; $Z^3$ is —COOH 76 mg of Zaragozic Acid A-3-methyl sulfonamide (from Example 5) in 1 mL of THF was stirred with 16 μL of DBU and 30 μL chloromethylpivalate at 50° C. for 2 days and the newly formed less polar product was purified by reverse phase HPLC (60/40 acetonitirle-water on C8 column).

$^1$H NMR (CD$_3$OD, 400 MHz) δ7.3–7.12 (m, 5H), 6.84 (dd, J=15.7, 9, Hz 1H), 6.10 (d, J=1.88 Hz, 1H), 5.9–5.7 (m, 3H), 5.20 (s, 1H), 4.84 and 4.82 (ea s, ea 1H), 4.07 (d, J=1.8 Hz, 1H), 3.22 (s, 3H), 2.6–2.15 (m, 5H), 2.10 (s, 3H), 1.4–1.1 (m, 5H), 1.20 (3, 9H), 1.02 (d, 7 Hz, 3H), 0.88 (m, 9H).

EXAMPLE 7

Preparation of Zaragozic Acid A-3-phenylsulfonamide (Compound of formula IA wherein $Z^1$ is CONHSO$_2$Ph; $Z^2=Z^3=$—COOH)

This compound was prepared as described in Examples 1–6 by using benzensulfonamide instead of methylsulfonamide.

$^1$H NMR (CD$_3$OD, 400 MHz) δ8.3–7.12 (m, 10H), 6.842 (dd, J=15.7, 9, Hz 1H), 6.18 (br s, 1H), 5.78 (d, J=15.7, 1H), 5.08 (d, J=5.4 Hz, 1H), 5.06 and 5.02 (ea s, ea 1H), 4.04 (s, 1H), 2.6–2.15 (m, 5H), 2.10 (s, 3H), 1.4–1.1 (m, 5H), 1.02 (d, 7 Hz, 3H), 0.95–0.88 (m, 9H).

EXAMPLE 8

Preparation of Zaragozic Acid A-3-phenyl sulfonamide-4-methylpivalate (Compound of formula IA wherein $Z^1$ is CONHSO$_2$Ph; $Z^2$ is —COOCH$_2$OC(O)C(CH$_3$)$_3$; $Z^3$ is —COOH)

This compound was prepared as shown above for "A"-3-methylsulfonamide-4-POM ester by using "A"-3-phenylsulfonamide instead of "A"-3-methylsulfonamide.

$^1$H NMR (CD$_3$OD, 400 MHz) δ8–7.12 (m, 10H), 6.84 (dd, J=16, 9, Hz 1H), 6.02 (s, 1H), 5.8–5.75 (m, 3H), 5.1–5.0 (m, 3H), 4.03 (s, 1H), 2.6–2.15 (m, 5H), 2.10 (s, 3H), 1.4–1.1 (m, 5H), 1.16 (3, 9H), 1.02 (d, 7 Hz, 3H), 0.9–0.82 (m, 9H).

EXAMPLE 9

Preparation of "A"-3-(4-chlorophenylsulfonamide) (Compound of formula IA wherein $Z^1$ is —CONHSO$_2$-(4-chlorophenyl); $Z^2=Z^3=$—COOH)

Step 1: Preparation of "A"-3-(4-chlorophenylsulfonamide)-4,5-di-t-butyl ester

Two 10 ml pear shaped flasks were equipped with triangular stirring vanes and rubber septa. One flask was charged with 61 mg of "A"-4,5-di-t-butyl ester. The substrate was dissolved in 1 ml of dry (KF=92) methylene chloride. The flask was cooled to −20° C. and charged with 9.20 μl of N-methylmorpholine. The reaction was allowed to warm slowly to −5° C. over a 15 min. period. The reaction was recooled to −20° C. and treated with 10.3 μl of isobutyl chloroformate. The flask was allowed to warm slowly to −5° C. over a 15 min. period and stirred at that temperature for an additional 15 min.

The second flask was charged with 15.3 mg of 4-chlorophenylsulfonamide followed by 1 ml of dry (KF=47) THF. The mixture was stirred at ambient temperature until dissolution was complete. The flask was cooled to 0° C. and charged with 11.9 μl of DBU. The solution was stirred at 0° C. for 10 min.

The first flask was cooled to −20° C. The contents of the second flask were transferred to the first flask by Gastight syringe. The homogenous reaction mixture was stirred at −20° C. for 1 hour, then allowed to warm slowly in the cold bath until ambient temperature was reached. Stirring was continued until HPLC analysis showed no further progress (5 days).

At the end of this time the homogenous reaction mixture was poured into excess isopropyl acetate and washed once with pH7 buffer. The organic was dried over sodium sulfate, filtered and stripped to a yellow oil. The oil was chromatographed over silica gel. The mobile phase was initially 50% hexane/ethyl acetate. As the chromatography progressed the mobile phase was changed to 100% ethyl acetate. All fractions shown by LC to contain a major new product were collected and stripped to a residue. The partially purified product was rechromatographed with 4% MeOH in methylene chloride. Only the fractions containing uncontaminated product were collected and concentrated to a pale yellow oil of "A"-4,5-di-t-butyl-3-(4-chlorophenylsulfonamide). Analytical LC was performed on a Zorbax ODS 5u column (250 mm×4.6 mm). A gradient was employed as follows: Time(T in minutes)=0, %

CH$_3$CN=70, % H$_2$O=30; T=15, % CH$_3$CN=100. Flow=1.5 ml/min. Wavelength=210 nm. Retention times in minutes: "A"-4,5-di-t-butyl ester=12.00±0.2; product=16.45±0.2. NMR (400 MHz, CDCl3) δ8.84 (s, broad; 1H), 7.95 (d, J=8.8 Hz, 2H), 7.44 (d, J=8.9 Hz, 2H), 7.15-7.27 (m, 3H), 7.11 (d, J=6.9 Hz, 2H), 6.88 (dd, J=15.7, 8.4 Hz, 1H), 5.85 (d, J=1.9 Hz, 1H), 5.72 (d, J=15.8 Hz, 1H), 5.00-5.12 (m, 3H), 5.02 (s, broad; 1H), 3.98 (d, J=2.0 Hz, 1H), 3.79 (s, broad; 1H), 2.66 (dd, J=13.5, 6.2 Hz, 1H), 2.40 (dd, J=13.3, 8.6 Hz, 1H), 2.01-2.35 (m, 7H), 2.12 (s, 3H), 1.52 (s, 9H), 1.41 (s, 9H), 1.20 (d, J=6.5 Hz, 3H), 1.01 (d, J=6.6 Hz, 3H), 0.85 (d, J=6.8 Hz, 3H).

Step 2: Preparation of "A"-3-(4-chlorophenylsulfonamide)

A 10 ml pear shaped flask was equipped with a triangular stirring vane and rubber septum. The flask was charged with 5.7 mg of "A"-3-(4-chlorophenylsulfamoyl)carbonyl-4,5-bis(t-butyl)ester followed by 1 ml of dry methylene chloride (KF=104). The mixture was stirred at 25° C. until dissolution was complete. The flask was cooled to 0° C. and charged with 40 μl of trifluoroacetic acid. The reaction was allowed to warm slowly overnight in the cold bath. LC analysis indicated complete consumption of the substrate and the appearance of a new product. All volatile components were removed under high vacuum to give a partially granular white foam. LC analysis was carried out on a Zorbax ODS 5u analytical column (250 mm×4.6 mm). A gradient was employed as follows: Time (T in minutes=0, % CH$_3$CN=70, % H$_2$O=30; T=15, % CH$_3$CN=100. Flow=1.5 ml/min. Wavelength=210 nm. Retention times: starting material=16.45±0.2, desired product=10.26±0.2. NMR (400 MHz, CD$_3$OD) δ7.98 (d, J=8.7 Hz, 2H), 7.59 (d, J=8.7 Hz, 2H), 7.24-7.28 (m, 3H), 7.13-7.19 (m, 3H), 6.85 (dd, J=15.7, 8.6 Hz, 1H), 6.25 (d, J=1.8 Hz, 1H), 5.77 (d, J=15.5 Hz, 1H), 5.00-5.13 (m, overlapping H$_2$O from solvent, 4H), 4.06 (d, J=1.9 Hz, 1H), 2.69 (dd, J=13.3, 6.3 Hz, 1H), 2.18-2.48 (m, 7H), 2.12 (s, 3H), 2.01-2.10 (m, 3H), 1.42-1.62 (m, 6H), 1.12-1.17 (m, 3H), 1.09 (d, J=6.6 Hz, 3H), 1.00 (d, J=6.7 Hz, 3H), 0.88 (d, J=6.8 Hz, 3H).

EXAMPLE 10

Preparation of "A"-3-Hydroxamic acid (Compound of formula IA wherein Z$^1$ is CONHOH; Z$^2$=Z$^3$=—COOH)

Carbonyldiimidazole (229.1 mg) was added to "A"-7-(1-methoxy-1-methylethyl ether)-4,5-di-t-butyl ester (1.03 g) in DMF (6.8 mL) at −10° C. under nitrogen. After stirring for two hours triethyl amine (0.49 mL) was added followed by hydroxylamine (98.2 mg) and the mixture was allowed to warm up gradually to room temperature and stirred for additional three hours. After quenching with aqueous NaH$_2$PO$_4$ and standard extractive workup with ethyl acetate, the crude oil obtained was purified by preparative TLC on silica gel (ethyl acetate/hexane, 8/2 by volume) to give "A"-4,5-di-t-butyl-3-hydroxamic acid.

$^1$H NMR (400 MHz, CD$_3$OD) δ7.28-7.15 (m, 5H), 6.89 (dd, J=8.58, 15.68 Hz, 1H), 6.42 (d, J=1.84 Hz, 1H), 5.81 (d, J=15.68 Hz, 1H), 5.26 (s, 1H), 5.05 (d, J=4.89 Hz, 1H), 5.04 and 4.89 (ea s, ea 1H), 4.10 (d, J=1.84, 1H), 2.63 (dd, J=5.2, 13.2 Hz, 1H), 2.5-2.2 (m), 2.11 (s, 3H), 2.01 (m, 2H), 1.62 and 1.42 (ea s, ea 9H), 1.5-1.1 (m), 1.02 (d, J=6.69 Hz, 3H), 0.9-0.84 (m 9H).

Deprotection of the t-butyl groups was done with TFA in methylene chloride, followed by HPLC purification on C8 reverse phase column (acetonitrile-water) to give pure "A"-3-hydroxamic acid. $^1$H NMR (400 MHz, CD$_3$OD) δ7.32-7.12 (m, 5H), 6.85 (dd, J=8.76, 15.67 Hz, 1H), 6.28 (br s, 1H), 5.79 (d, J=15.67, 1H), 5.23 (br s, 1H), 5.05 (d, J=4.98 Hz, 1H), 5.03 and 4.97 (ea s, ea 1H), 4.04 (br s, 1H), 2.68 (dd, J=5.2, 13.2 Hz, 1H), 2,5-2.13 (m), 2.10 (s, 3H), 2.02 (m, 2H), 1.5-1.07 (m), 1.02 (d, J=6.64 Hz, 3H), 0.9-0.84 (m 9H); ms neg-FAB m/z 704.

EXAMPLE 11

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

cl EXAMPLE 12

Preparation of an Ammonium Salt

A 0.1 mmol sample of the free acid of Compound (I) is dissolved in 10 ml of ethyl acetate. The resulting solution is saturated with gaseous ammonia, upon which the ammonium salt precipitates from solution.

EXAMPLE 13

Preparation of Potassium Salt

A solution of 0.1 mmol of the free acid of Compound (I) in 10 ml of methanol is treated with an aqueous or methanolic solution containing 0.2 mmol of potassium hydroxide. Evaporation of the solvent affords the di-potassium salt. Addition of between 0.1 and 0.2 mmol of potassium hydroxide yields analogously mixtures of the mono-potassium and di-potassium salts whose composition depends upon the exact amount of potassium hydroxide added.

In a similar fashion, the sodium and lithium salts of Compound (I) can be formed.

EXAMPLE 14

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 15

Preparation of an ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N'-dibenzylethylenediamine salt.

EXAMPLE 16

Preparation of a Tris(hydroxymethyl)aminomethane salt

To a solution of 0.1 mmol of the free acid of a Compound of formula (I) in 10 ml of methanol is added from 0.1 to 0.2 mmol of tris(hydroxymethyl)aminomethane dissolved in 10 ml of methanol. Evaporation of the solvent gives a corresponding salt form of Compound (I) exact composition of which is determined by the molar ratio of amine added.

The method can also be applied to other amines such as, but not limited to: diethanolamine and diethylamine.

EXAMPLE 17

The preparation of a L-arginine salt

To a solution of 0.1 mmol of the free acid of a compound of formula (I) in 10 ml of 6:4 methanol/water is treated with an aqueous solution of 0.1-0.2 mmol of L-arginine. Evaporation of the solvent affords the title salt, the exact composition of which is determined by the molar ratio of amino acid to the free acid of Compound (I).

Similarly prepared are the salts of L-ornithine, L-lysine, and N-methylglucamine.

What is claimed is:

1. A compound of structural formula (I)

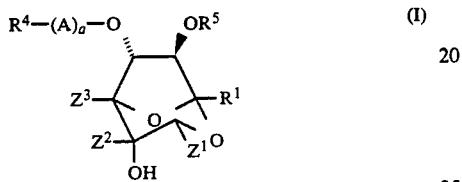

wherein

A is —C(O)—, —NR$^3$—C(O)—, or —OC(O)—;

a is zero or 1;

R$^1$ is selected from the group consisting of:
(1) C$_{1-20}$alkyl,
(2) substituted C$_{1-20}$alkyl in which one or more substituents is selected from a group herein termed X$^3$ wherein the group X$^3$ consists of:
  (a) halogen,
  (b) hydroxy,
  (c) R$^3$R$^3$N—,
  (d) R$^2$O—,
  (e) R$^2$O—C(O)—,
  (f) R$^3$—C(O)—O—,
  (g) oxo,
  (h) C$_{3-10}$cycloalkyl,
  (i) aryl substituted with X and Y,
  (j) heteroaryl substituted with X and Y,
  (k) heterocycloalkyl,
  (l) aryl S(O)$_n$, wherein aryl is substituted with X and Y,
  (m) R$^3$—C(O)—NR$^3$—,
  (n) R$^3$R$^3$N—C(O)—,
  (o) —CO$_2$H,
  (p) —vinylidene,
  (q) R$^3$—C(O)—,
  (r) R$^2$O—C(O)—O—,
  (s) R$^3$R$^3$N—C(O)—O—, and
  (t) R$^2$O—C(O)—NR$^3$—;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O— or —S(O)$_n$— and wherein one or more carbon substituents is selected from the group X$^3$, defined above;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the saturated carbons is substituted with a substituent selected from the group X$^3$, defined above;
(9) C$_{2-20}$alkenyl wherein alkenyl contains one or more double bonds and one or more of the nonolefinic carbons is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more of the saturated carbons is substituted with a substituent selected from the group X$^3$, defined above;
(11) C$_{3-10}$cycloalkyl;
(12) substituted C$_{3-10}$cycloalkyl in which one or more of the substituents is selected from the group consisting of C$_{1-10}$alkyl—S(O)$_n$—, C$_{1-10}$alkyl, and the members of the group X$^3$, defined above;

each R$^2$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl— wherein heteroaryl is substituted with X and Y;
(6) heterocycloalkylC$_{1-4}$alkyl—;
(7) C$_{2-10}$alkenyl;
(8) arylC$_{2-10}$alkenyl wherein aryl is substituted with X and Y; and
(9) C$_{3-10}$alkynyl;

each R$^3$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl— wherein heteroaryl is substituted with X and Y;
(6) heterocycloalkylC$_{1-4}$alkyl—;
(7) C$_{2-10}$alkenyl;
(8) arylC$_{2-10}$alkenyl wherein aryl is substituted with X and Y;
(9) C$_{3-10}$alkynyl;
(10) hydrogen; and
(11) C$_{1-5}$alkyl substituted with X$^1$;

R$^4$ is selected from the group consisting of:
(1) C$_{1-20}$alkyl;
(2) substituted C$_{1-20}$alkyl in which one or more substituents is selected from the group X$^3$, defined above;
(3) C$_{1-20}$alkyl wherein one or more of the carbons is replaced by —NR$_3$—, —O—, or —S(O)$_n$—;
(4) substituted C$_{1-20}$alkyl wherein one or more of the carbons is replaced by —NR$^3$—, —O— or —S(O)$_n$— and wherein one or more carbon substituents is selected from the group X$^3$, defined above;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the saturated carbons is substituted with a substituent selected from the group $X^3$, defined above;

(9) $C_{2-20}$alkenyl wherein alkenyl contains one or more double bonds and one or more of the nonolefinic carbons is replaced by $-NR^3-$, $-O-$ or $-S(O)_n-$;

(10) substituted $C_{2-20}$alkenyl wherein alkenyl contains one or more double bonds and one or more of the nonolefinic carbons is replaced by $-NR^3-$, $-O-$ or $-S(O)_n-$ and wherein one or more of the saturated carbons is substituted with a substituent selected from the group $X^3$, defined above;

(11) $C_{3-10}$cycloalkyl;

(12) substituted $C_{3-10}$cycloalkyl in which one or more of the substituents is selected from the group $X^3$, defined above; and

(13) hydrogen;

$R^5$ is selected from the group consisting of:
(1) hydrogen;
(2) $C_{1-10}$alkyl;
(3) aryl substituted with X and Y;
(4) aryl$C_{1-4}$alkyl, wherein aryl is substituted with X and Y;
(5) $R^2O-C(O)-$;
(6) $C_{3-10}$cycloalkyl;
(7) $R^3-C(O)-$; and
(8) $R^3R^3N-C(O)-$;

n is zero, 1 or 2;
$Z^1$ is selected from:
(1) $-CONHOH$,
(2) $-CONHSO_2R$, and
(3) tetrazolyl;
$Z^2$ is $-CO_2R^6$;
$Z^3$ is
R is selected from:
(1) $C_{1-10}$alkyl,
(2) phenyl substituted with X and Y,
(3) $C_{1-10}$alkyl substituted with phenyl, wherein the phenyl is substituted with X and Y, and
(4) heteroaryl substituted with X and Y;

$R^6$ is independently selected at each occurrence from the group consisting of:
(1) $C_{1-20}$alkyl;
(2) substituted $C_{1-20}$alkyl in which one or more substituents is selected from the group $X^3$, defined above,
(3) $C_{1-20}$alkyl wherein one or more of the carbons is replaced by $-NR^3-$, $-O-$, or $-S(O)_n-$;
(4) substituted $C_{1-20}$alkyl wherein one or more of the carbons is replaced by $-NR^3-$, $-O-$, or $-S(O)_n-$ and wherein one or more carbon substituents is selected from the group $X^3$, defined above;
(5) $C_{2-20}$alkenyl wherein alkenyl contains one or more double bonds;
(6) substituted $C_{2-20}$alkenyl wherein alkenyl contains one or more double bonds and wherein one or more of the saturated carbons is substituted with a substituent selected from the group $X^3$, defined above;
(7) $C_{2-20}$alkenyl wherein alkenyl contains one or more double bonds and one or more of the nonolefinic carbons is replaced by $-NR^3-$, $-O-$, or $-S(O)_n-$;
(8) substituted $C_{2-20}$alkenyl wherein alkenyl contains one or more double bonds and one or more of the nonolefinic carbons is replaced by $-NR^3-$, $-O-$, or $-S(O)_n-$ and wherein one or more of the saturated carbons is substituted with a substituent selected from the group $X^3$, defined above;

(9) $C_{2-20}$alkynyl wherein alkynyl contains one or more triple bonds;

(10) substituted $C_{2-20}$alkynyl wherein alkynyl contains one or more triple bonds and wherein one or more of the saturated carbons is substituted with a substituent selected from the group $X^3$, defined above;

(11) $C_{2-20}$alkynyl wherein alkynyl contains one or more triple bonds and one or more of the saturated carbons is replaced by $-NR^3-$, $-O-$, or $-S(O)_n-$;

(12) substituted $C_{2-20}$alkynyl wherein alkynyl contains one or more —triple bonds— and one or more of the saturated carbons is replaced by $-NR^3-$, $-O-$, or $-S(O)_n-$ and wherein one or more of the saturated carbons is substituted with a substituent selected from the group $X^3$, defined above;

(13) aryl substituted with X and Y;
(14) heteroaryl substituted with X and Y;
(15) $C_{3-5}$cycloalkyl;
(16) substituted $C_{3-5}$cycloakyl in which one or more of the substituents is selected from:
   (a) $R^3O-$, and
   (b) $R^3R^3N-$; and
(17) hydrogen;

aryl including X, Y substitution is:

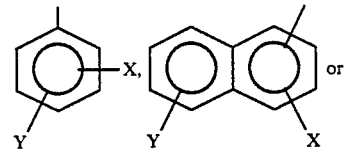

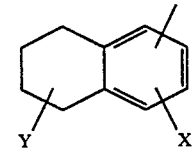

heteroaryl including X, Y substitution is selected from

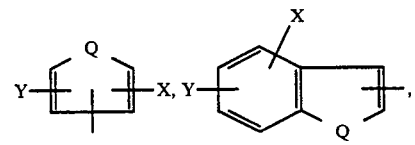

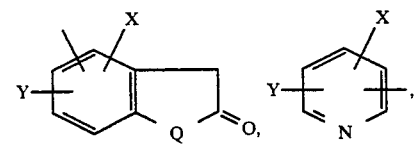

-continued

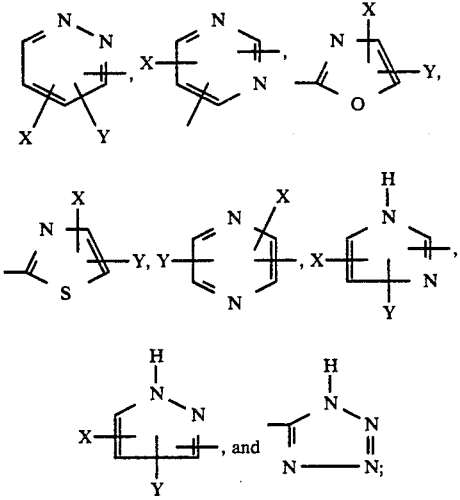

wherein:
Q is —NR$^3$, —O— or —S—;
heterocycloalkyl is selected from:

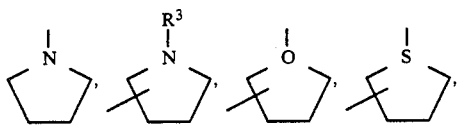

wherein:

M is —NR$^3$, —O—, —S— or —CH$_2$—;
X and Y are each independently selected from:
(1) hydrogen;
(2) hydroxy;
(3) halogen;
(4) trifluoromethyl;
(5) C$_{1-10}$alkyl;
(6) aryl substituted with X$^1$ and Y$^1$;
(7) R$^2$O—;
(8) arylcarbonyloxy—, wherein aryl is substituted with X$^1$ and Y$^1$;
(9) R$^3$—C(O)—O—;
(10) —CO$_2$R$^2$;
(11) —CO$_2$H; and
(12) nitro; and
X$^1$ and Y$^1$ are each independently selected from:
(1) hydrogen;
(2) hydroxy;
(3) halogen;
(4) trifluoromethyl;
(5) C$_{1-4}$alkyl;
(6) R$^2$O—;
(7) R$^3$—C(O)—O—;
(8) —CO$_2$R$^2$;
(9) —CO$_2$H; and
(10) nitro;
or the pharmaceutically acceptable salt thereof.

2. The compound of claim 1 having a structural formula selected from

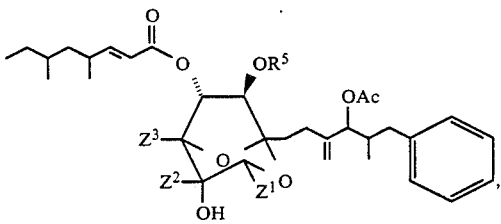

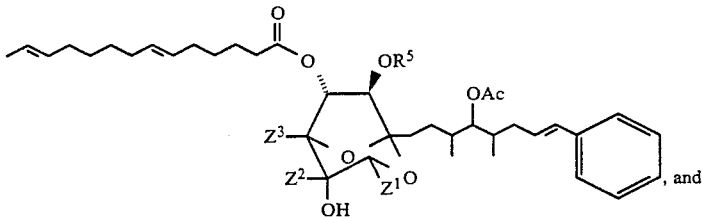

, and

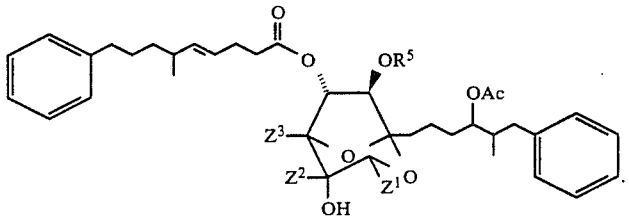

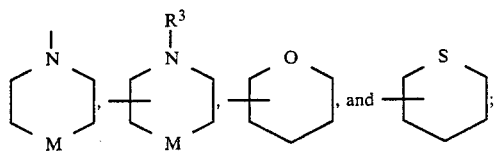

3. The compound of claim 2 having the structural formula

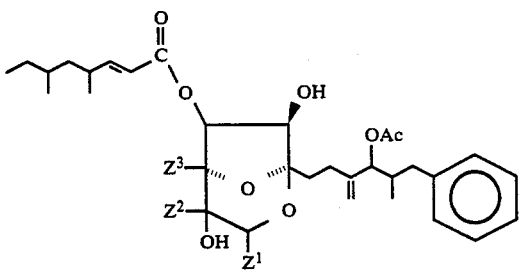

wherein
$Z^1$ is selected from the group consisting of
(a) —CONHSO$_2$R and
(b) —CONHOH;
R is selected from the group consisting of
(a) C$_{1-10}$ alkyl,
(b) phenyl substituted with X and Y, and
(c) heteroaryl substituted with X and Y;
X and Y are each independently selected from
(a) hydrogen,
(b) C$_{1-5}$ alkyl,
(c) —CO$_2$H,
(d) C$_{1-5}$ alkoxy,
(e) nitro,
(f) halogen, and
(g) —S(O)$_n$ C$_{1-5}$alkyl, n=0, 1, 2;
$Z^2$ and $Z^3$ are each —CO$_2$R$^6$; and
R$^6$ is independently selected at each occurence from
(a) H,
(b) C$_{1-5}$ alkyl, and
(c) C$_{1-5}$ alkyl substituted with a member of the group consisting of IA
(i) phenyl,
(ii) phenyl substituted with methyl, methoxy, halogen (cl, Br, I, F) or hydroxy, and
(iii) C$_{1-5}$ alkylcarbonyloxy.

4. The compound of claim 3 wherein $Z^1$ is —CONHSO$_2$R or —CONHOH, R is methyl or phenyl substituted with X and Y, and X and Y are independently selected from hydrogen and halogen.

5. The compound of claim 4 wherein R$^6$ is independently selected at each occurrence from
(a) hydrogen,
(b) C$_{1-5}$ alkyl, and
(c) C$_{1-5}$ alkyl substituted with C$_{1-5}$ alkyl carbonyloxy.

6. The compound of claim 5 wherein R$^6$ is hydrogen at each occurrence.

7. The compound of claim 6 wherein $Z^1$ is —CONHSO$_2$R, and R is methyl.

8. The compound of claim 6 wherein $Z^1$ is —CONHSO$_2$R, R is phenyl and X and Y are each hydrogen.

9. The compound of claim 6 wherein $Z^1$ is —CONHSO$_2$R, and R is 4-chlorophenyl.

10. The compound of claim 6 wherein $Z^1$ is —CONHOH.

11. The compound of claim 5 wherein at least one of R$^6$ is —CH$_2$OC(O)C(CH$_3$)$_3$.

12. The compound of claim 11 wherein $Z^1$ is —CONHSO$_2$R, $Z^2$ is —COOCH$_2$OC(O)C(CH$_3$)$_3$, $Z^3$ is —COOH, and R is methyl.

13. The compound of claim 11 wherein $Z^1$ is —CONHSO$_2$R, $Z^2$ is —COOCH$_2$OC(O)C(CH$_3$)$_3$, $Z^3$ is —COOH and R is phenyl.

14. A pharmaceutical composition comprising a compound of claim 1 and a pharmaceutically acceptable carrier.

* * * * *